United States Patent
Sims et al.

[11] Patent Number: 5,992,212
[45] Date of Patent: *Nov. 30, 1999

[54] DEVICE FOR DETERMINING COEFFICIENT OF FRICTION AND LEVEL OF LUBRICATION

[75] Inventors: Roger D. Sims, Munster; Keith A. Miller, Schererville; Gilbert F. Schepmann, Jr., Valparaiso, all of Ind.

[73] Assignee: Roger D. Sims, P.E., Munster, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/964,852

[22] Filed: Nov. 5, 1997

Related U.S. Application Data
[60] Provisional application No. 06/029,884, Nov. 7, 1996.

[51] Int. Cl.⁶ .................................................. G01N 19/02
[52] U.S. Cl. .......................................... 73/8; 73/9
[58] Field of Search .................. 73/7, 8, 9, 10, 73/104, 105, 862.041, 862.042, 862.043, 862.044

[56] References Cited

U.S. PATENT DOCUMENTS

| | | | |
|---|---|---|---|
| 2,821,081 | 1/1958 | Staples | 73/105 |
| 3,992,922 | 11/1976 | Noble | 73/9 |
| 3,993,270 | 11/1976 | Gallacher | 73/9 |
| 4,051,713 | 10/1977 | Bao et al. | 73/9 |
| 4,484,666 | 11/1984 | Steinmetz et al. | 188/165 |
| 4,594,878 | 6/1986 | Abe et al. | 73/9 |
| 4,712,431 | 12/1987 | Hatamura | 73/862.044 |
| 4,722,218 | 2/1988 | Strader | 73/9 |
| 4,813,266 | 3/1989 | Nash | 73/9 |
| 4,958,512 | 9/1990 | Johnsen | 73/9 |

OTHER PUBLICATIONS

Sims, Roger D., Miller, Keith A. and Schepmann Jr., Gilbert F., "Rail Lubrication Measurement", ASME/IEEE Joint Railroad Conference, Oak Brook, Illinois, Apr. 30–May 2, 1996.

*Primary Examiner*—Max Noori
*Attorney, Agent, or Firm*—Marshall, O'Toole, Gerstein, Murray & Borun

[57] ABSTRACT

An apparatus for determining a coefficient of friction on a surface of objects such as rails. In one embodiment, the apparatus comprises a vertical sensor assembly for determining the coefficient of friction of a top surface of a rail. A different embodiment comprises a lateral sensor assembly for determining a coefficient of friction of a gage face of a rail. The sensor assemblies may include a shoe. The sensor assemblies may include a load cell. Other embodiments include various combinations of lateral sensor assemblies and vertical sensor assemblies. Structure for mounting the assemblies to a vehicle may also be provided.

25 Claims, 7 Drawing Sheets

DIRECTION OF TRAVEL

FIGURE 3

DIRECTION OF TRAVEL

DEVICE FOR DETERMINING COEFFICIENT OF FRICTION AND LEVEL OF LUBRICATION

This application claims the benefit of U.S. provisional application No. 60/029,884, filed Nov. 7, 1996.

BACKGROUND OF THE INVENTION

This invention relates generally to devices for measuring the coefficient of friction between a sliding piece and a stationary element, and in particular to a device adapted for measuring the coefficient of friction of railroad rail.

Railroad rails are lubricated primarily for two reasons: reduction of wear and reduction of energy consumption. While lubrication has been used on rails in curves for decades, recent discoveries have made it advantageous to lubricate straight or tangent track to reduce locomotive fuel consumption. Conversely, there are some operating situations where lubrication is very undesirable because of a need for high traction by the locomotive and braking of entire trains. Management of lubrication strategies is essential to safe and efficient railroad operations.

A conventional device for measuring friction must be pushed along the track manually by an operator. It can only measure one location on one track at a time. Also, it is very labor-intensive and places the operator out in the elements while measurements are taken.

A device was needed that measured both the running surface (top) and the gage face (side) or corner of both rails. Such a device would preferably provide information on the lubrication condition of four locations as the device was moved along a pair of railroad tracks. Mounting of such a device on a regular piece of railroad maintenance and inspection equipment would increase its utility. The railroads regularly use a modified pickup truck with small railroad wheels attached to inspect railroad tracks. The small railroad wheels guide the pickup truck and its rubber tires provide the traction and motive power. The installation of a coefficient of friction measuring device on the front bumper of such a pickup truck would greatly enhance the utility of such a measuring device. The operator could place the friction measuring device on the rail and drive for miles, collecting data in the process. By using a computer up in the cab of the pickup with electrical connections to the friction measuring device, the operator could observe the electrical responses of the device and discern the actual coefficient of friction as he drives on the rail. The device could also record the measurements for later analysis.

An object of the invention is to provide a simple, accurate, reliable device with minimal maintenance to measure the coefficient of friction to assess lubrication levels. It would be advantageous to assess the levels of lubrication at two locations of both railroad tracks simultaneously. The device is preferably lightweight for ease of installation and easy to use. Preferably, it produces consistent results independent of travel speed or the vehicle to which it is attached. An advantage of the invention described herein is that a lightweight device can be easily mounted to a railroad maintenance vehicle and collect many miles of data reliably, which will enable improved management of rail lubrication on the railroads.

SUMMARY OF THE INVENTION

The aforementioned disadvantages of conventional devices are overcome by apparatus in accordance with the present invention. In particular, one embodiment of the present invention is an apparatus for determining a coefficient of friction of a rail surface. The apparatus comprises (1) a shoe biased against the rail surface, (2) means for sensing a tangential load, the tangential load sensing means contacting the shoe, and (3) means for sensing a normal load, the normal load being applied from the shoe to the surface of the rail.

Another embodiment of the present invention comprises a vertical sensor assembly for measuring lubrication of the top surface of a track. The vertical sensor assembly includes means for measuring normal and tangential loads through a shoe contacting a rail that allows for the measurement of the coefficient of friction.

A further embodiment of the present invention comprises a lateral sensor assembly for measuring lubrication of the gage of a track. The lateral sensor assembly includes means for measuring normal and tangential loads through a shoe contacting a rail that allows for measurement of the coefficient of friction. The lateral sensor assembly may be secured by a cross guard. The cross guard guides the lateral sensor assembly when rail features such as gaps are encountered.

The shoes preferably are shaped to pass over rail features such as gaps and to aid in guiding the sensor to the preferred position.

The sensor assemblies may be adapted to be mounted to a vehicle such as a high rail vehicle. A bracket, for example, may be used to mount a sensor assembly or assemblies upon a vehicle. Preferably, the sensor assemblies are mounted so that the assemblies may move laterally (i.e., perpendicular to the direction of the rails) independently of the lateral movement of the vehicle.

A further embodiment includes a lateral sensor assembly and a vertical sensor assembly connected by a base plate. This embodiment can measure lubrication virtually simultaneously on both the top surface of a track and the gage face of the track.

A still further embodiment includes first and second lateral sensor assemblies and first and second vertical sensor assemblies. Preferably, the assemblies are arranged so that the first lateral sensor assembly and the first vertical sensor assembly can measure lubrication on a first rail at the same time that the second lateral sensor assembly and the second vertical sensor assembly measure lubrication on a second rail. In this embodiment, the first lateral sensor assembly can be secured to a cross guard rod so that the shoe of the first lateral assembly does not become damaged when rail features such as gaps are encountered. Also preferably, the second lateral sensor assembly can be secured to a cross guard rod so that the shoe of the second lateral assembly properly guides when rail features such as gaps are encountered.

DETAILED DESCRIPTION OF THE INVENTION

Figure 4:
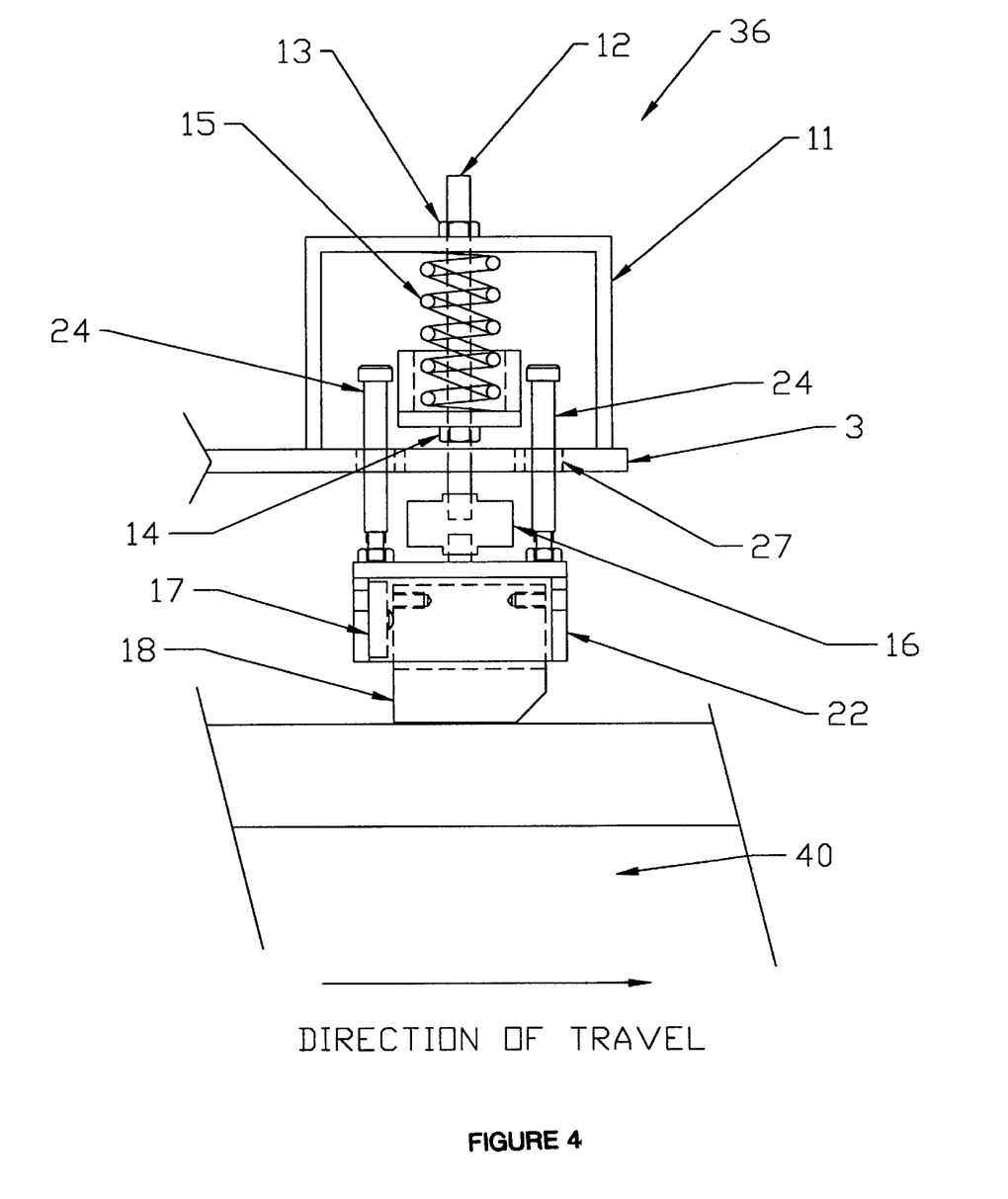
FIG. 4 is a side view of a vertical sensor assembly in accordance with the present invention shown without the main housing.

One embodiment of the present invention, best seen in FIG. 4, is a vertical sensor assembly comprising a shaft 12 that is attached to a normal load sensing device 16, such as a load cell or strain gage. The normal load sensing device 16 is attached to the vertical sensor shoe housing 22. Disposed inside the housing 22 is a shoe 18 and a tangential load sensing device 17, such as a load cell. The shoe 18 is mounted to the vertical shoe housing 22 to permit longitudinal movement (i.e., movement parallel to the tracks 40). The shoe 18 contacts the tangential load sensing device 17 while measurements are taken.

Figure 9A:
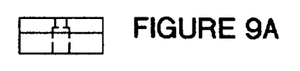
FIG. 9A is a front elevational view of an alternative vertical sensor shoe embodiment.
Figure 9B:
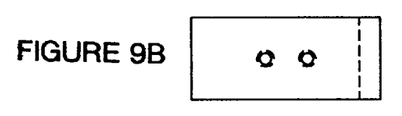
FIG. 9B is a plan view of the alternative vertical sensor shoe embodiment of FIG. 9A.
Figure 9C:
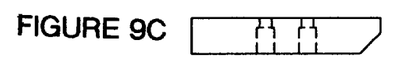
FIG. 9C is a side elevational view of the alternative vertical sensor shoe embodiment of FIG. 9A.
Figure 10A:
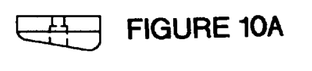
FIG. 10A is a front elevational view of an alternative vertical sensor shoe embodiment.
Figure 10B:
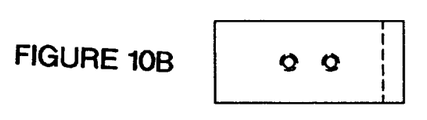
FIG. 10B is a plan view of the alternative vertical sensor shoe embodiment of FIG. 10A.
Figure 10C:
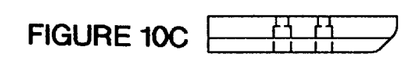
FIG. 10C is a side elevational view of the alternative vertical sensor shoe embodiment of FIG. 10A.

Some contours of the shoe 18 have advantages over other contours. For example, a shoe 18 shaped as shown in FIGS. 9A–9C can pass over most rail features including gaps. Preferably the shape of one or more pairs of shoes keeps the device in lateral alignment with the rails 40 independent of the vehicle's lateral alignment. The shoe 18 may be of any shape that will allow for passage over the top surfaces of rails 40. Such shoes are shown in FIGS. 9A–11C.

Figure 11A:
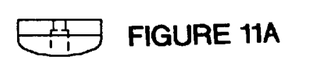
FIG. 11A is a front elevational view of an alternative vertical sensor shoe embodiment.
Figure 11B:
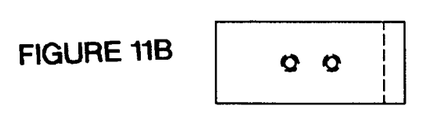
FIG. 11B is a plan view of the alternative vertical sensor shoe embodiment of FIG. 11A.
Figure 11C:
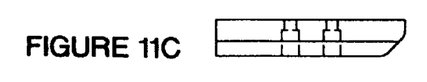
FIG. 11C is a side elevational view of the alternative vertical sensor shoe embodiment of FIG. 11A.

The alternate vertical shoe shapes shown in FIGS. 9A–11C have features that allow for passage over various rail features such as gaps. This is primarily accomplished by the tapers on the leading edge of the shoe as seen in FIGS. 9C, 10C and 11C. The length of the shoe also keeps the shoe from falling into gaps in the rail. The taper seen in FIG. 10A helps guide the unit into proper alignment and also helps control the location of the measurements. The taper seen in FIG. 11A allows for precise measurement location.

Referring again to FIG. 4, the shoe 18 is held in contact with the top surface of the rail 40 by an adjustable load device 15, shown as a compression spring, that is mounted around the shaft 12. In this case, the load may be adjusted using nuts 13 and 14 located above and below the spring 15, respectively. The shoe housing 22 is constrained from horizontal movement and is guided in the vertical direction by the vertical guides 24. Each of the vertical guides 24 slide in a low friction bushing 27.

The coefficient of friction, $\mu$, is determined through the use of the equation $F=\mu N$ where F is the tangential force and N is the normal force. These forces are obtained using the aforementioned load sensing devices 16, 17 simultaneously. The level of lubrication can be determined from $\mu$ because it typically is proportional to $\mu$, at least when comparing levels of a single type of lubrication agent.

Figure 5:
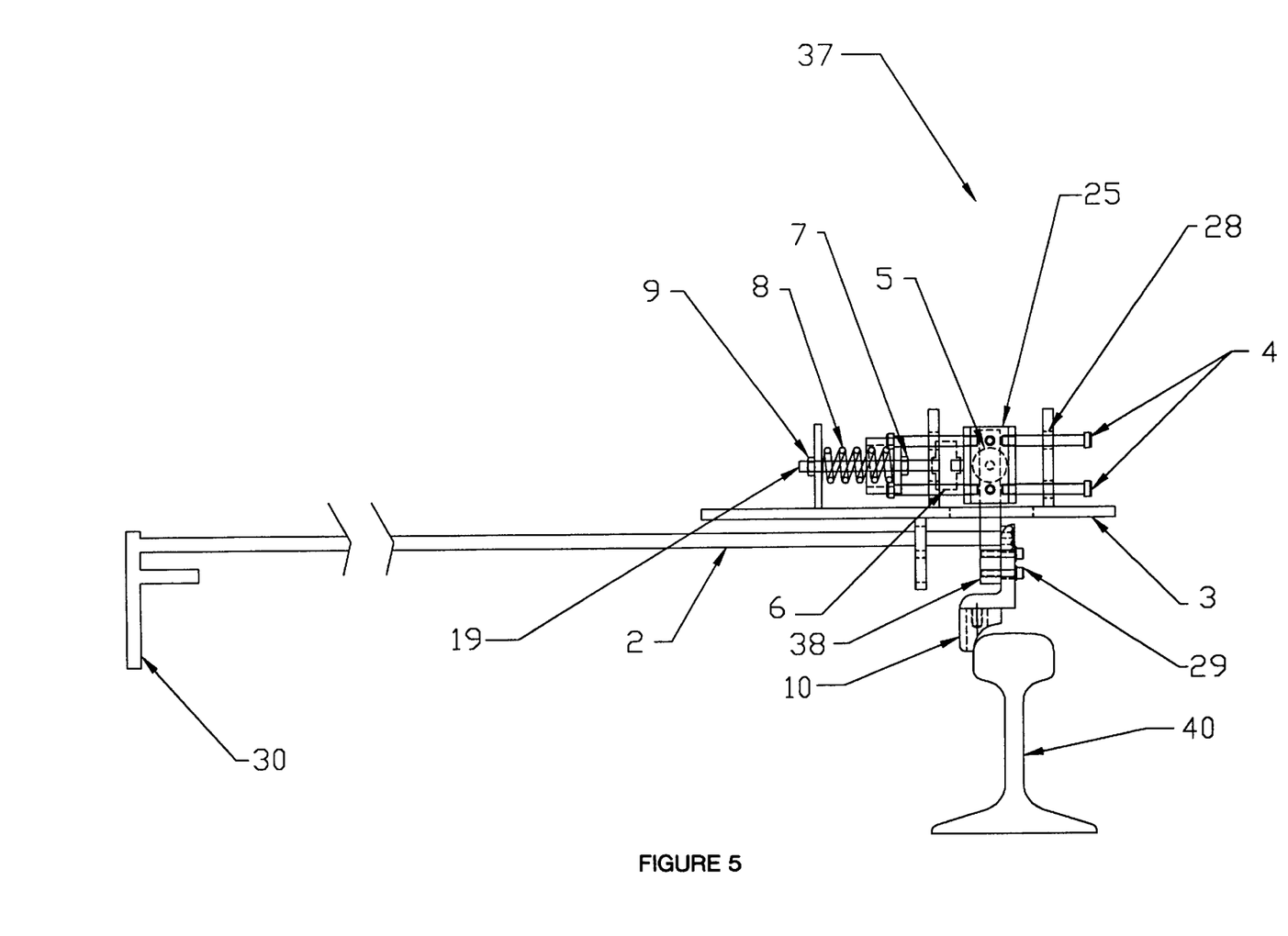
FIG. 5 is an elevational view of a lateral sensor assembly in accordance with the present invention shown without the main housing.

Another embodiment of the present invention, best seen in FIG. 5, is a lateral sensor assembly comprising a shaft 19 that is attached to a normal load sensing device 6, such as load cell or strain gage. The load sensing device 6 is attached to the lateral sensor shoe housing 25. Disposed inside the housing 25 is the lateral shoe connector plate 38 and a tangential load sensing device 5, such as a load cell. The shoe 10 is mounted to the lateral shoe connector plate 38 to permit longitudinal movement (i.e., movement parallel to the tracks). The shoe 10 contacts the load sensing device 5 while measurements are taken.

The shoe 10 may be of any shape that will allow for passage over rails 40. Preferably, the shape of one or more pairs of shoes keeps the device in lateral alignment with the gage face of the rail 40 independent of the vehicle's lateral alignment. Such a shoe is shown in FIGS. 7A–7C and 8A–8B.

The alternate lateral shoe shapes shown in FIGS. 7A–8B allow for easy transition over and through various rail crossings. The taper shown in FIG. 7C allows for smooth traversing across rail discontinuities. The cutout shown in FIG. 7A allows the shoe to conform to the rail corner and the inside of the rail. The taper on the shoe shown in FIG. 8B allows for easy entrance and exit of rail gaps. The curved shape shown in FIG. 8A allows the shoe to be easily adjusted vertically and be placed anywhere on the side of the rail.

Referring again to FIG. 5, the shoe 10 is held in contact with the rail gage face or side of rail by an adjustable load device 8, shown as a compression spring, that is mounted around the shaft 19. The load is adjusted by nuts 7 and 9 located on either side of the spring. The lateral sensor movement is restricted in the lateral direction (i.e., in a direction perpendicular to the direction of travel and in a plane intersecting both tracks), by the lateral guard rod 2 which is connected to the lateral guard vertical plate 38 and the lateral sensor housing 11. The lateral guard vertical plate 30 engages guards in the track work which prevents the shoe 10 from moving into gaps in crossings, frogs and switches. The shoe housing 25 is constrained vertically and is guided in the lateral direction by the lateral guides 4 which slide in low friction bushings 28. The shoe 10 is adjustable in the vertical direction by use of the lateral shoe vertical adjustment nut 29 to allow for measurements to be taken at any location from the upper corner of the rail 40 down to the inside surface of the rail 40.

Figure 6A:
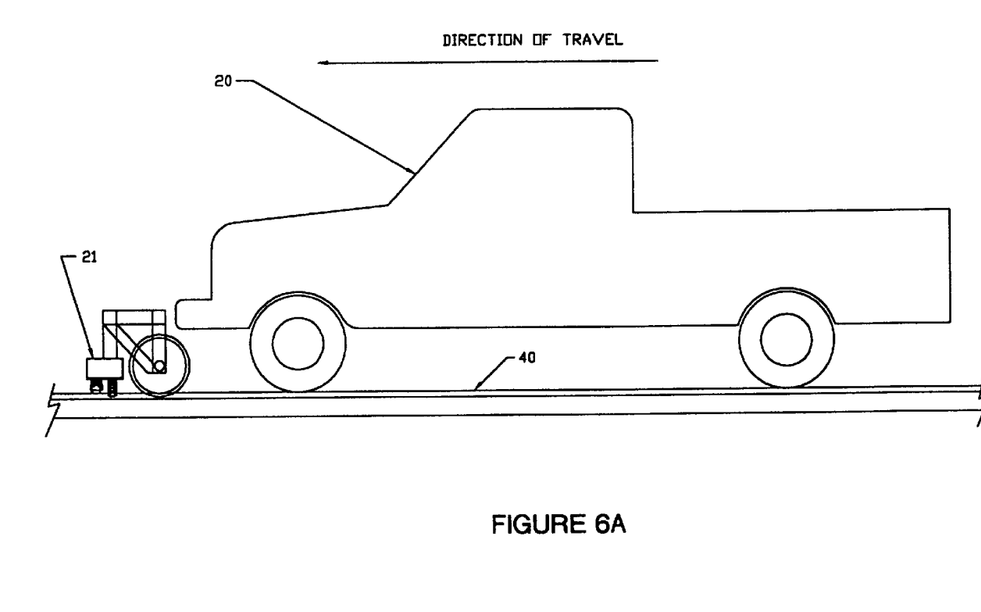
FIG. 6A is a side elevational view of an embodiment of the present invention shown attached to a high rail vehicle.
Figure 6B:
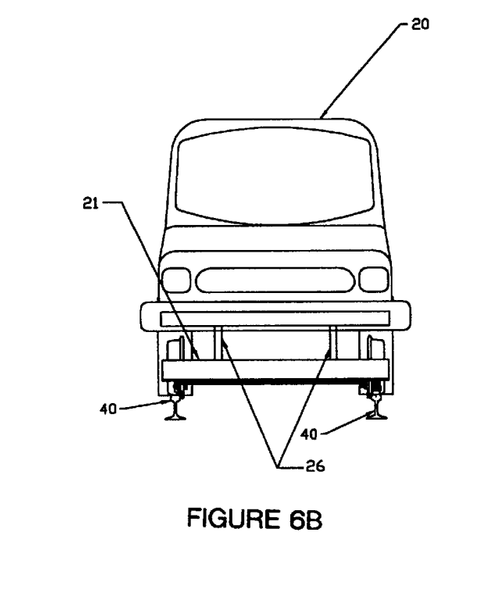
FIG. 6B is a front elevational view of the embodiment of FIG. 6A.
Figure 7A:
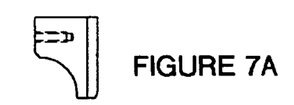
FIG. 7A is a front elevational view of an alternative lateral sensor shoe embodiment.
Figure 7B:
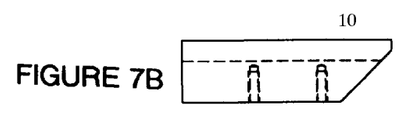
FIG. 7B is a plan view of the alternative lateral sensor shoe embodiment of FIG. 7A.
Figure 7C:
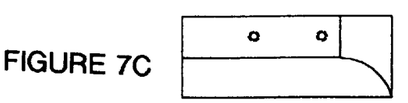
FIG. 7C is a side elevational view of the alternative lateral sensor shoe embodiment of FIG. 7A.
Figure 8A:
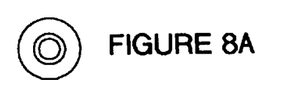
FIG. 8A is a front elevational view of an alternative lateral sensor shoe embodiment.
Figure 8B:
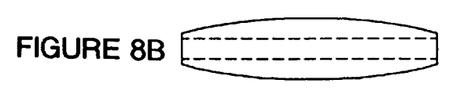
FIG. 8B is a plan view of the alternative lateral sensor shoe embodiment of FIG. 8A.

As seen in FIGS. 6A and 6B, the device 21 may be rigidly mounted to a vehicle 20, shown as a high rail vehicle, by means of the brackets 26 or any other suitable means. A high rail vehicle comprises a pickup truck outfitted with small railroad wheels. The device 21 is allowed to move laterally, independent of movement of the vehicle 20. The vehicle 20 propels the device 21 over the tracks 40 or other surfaces to be measured.

The load sensing devices 16, 17, 5 and 6 are attached to any suitable type of electronic data collection device (not shown). The data collection device may include signal conditioners, an analog-to-digital convertor and a personal computer.

Figure 3:
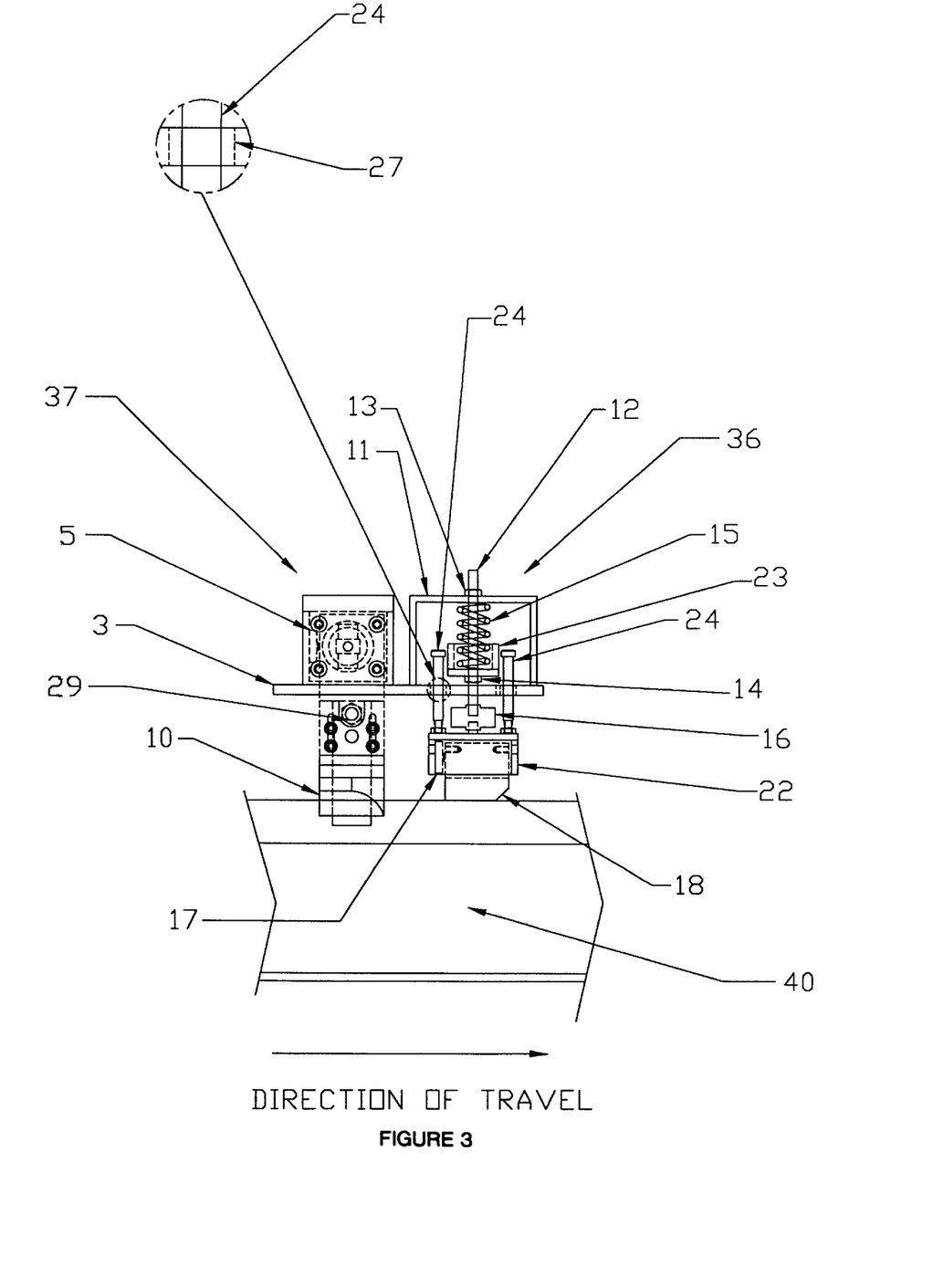
FIG. 3 is side elevational view of an embodiment of the present invention shown without a main housing.

In a further embodiment, best seen in FIG. 3, a lateral sensor assembly 37 and a vertical sensor assembly 36 are connected by the base plate 3 or any other suitable connection structure. In this embodiment, lubrication measurements may be made simultaneously for both the top surface of the rail and the gage face or side of rail 40.

Figure 1:
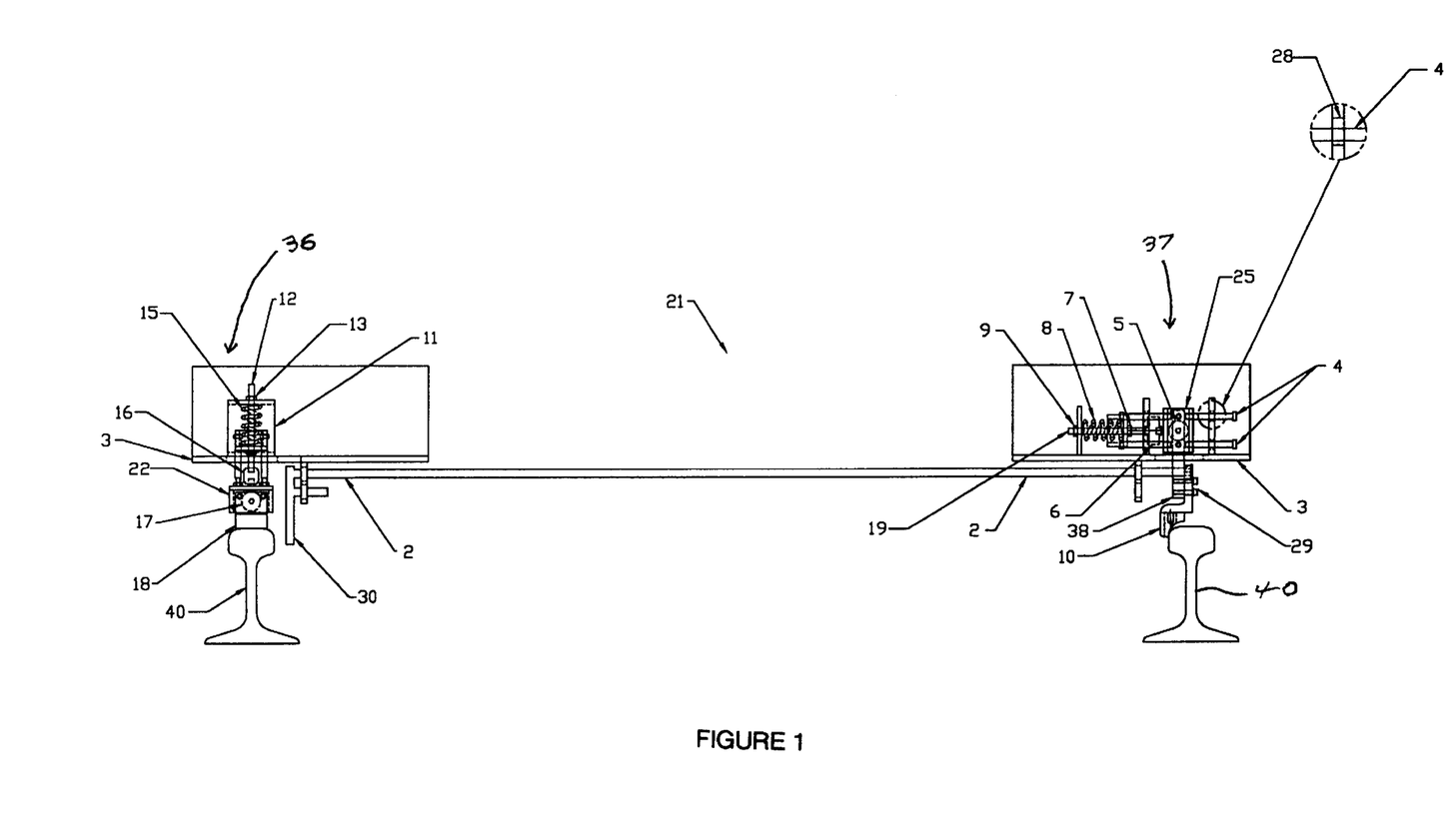
FIG. 1 is a front elevational view of an embodiment of the present invention shown without a main housing.

FIG. 1 shows an embodiment comprising a vertical sensor assembly 36 on a first rail 40 and a lateral sensor assembly 37 on a second rail 40. The assemblies 36, 37 are connected by a suitable structure such as an aluminum frame. This embodiment makes at least one friction measurement (i.e., top surface and/or gage face) on each rail 40.

Figure 2:
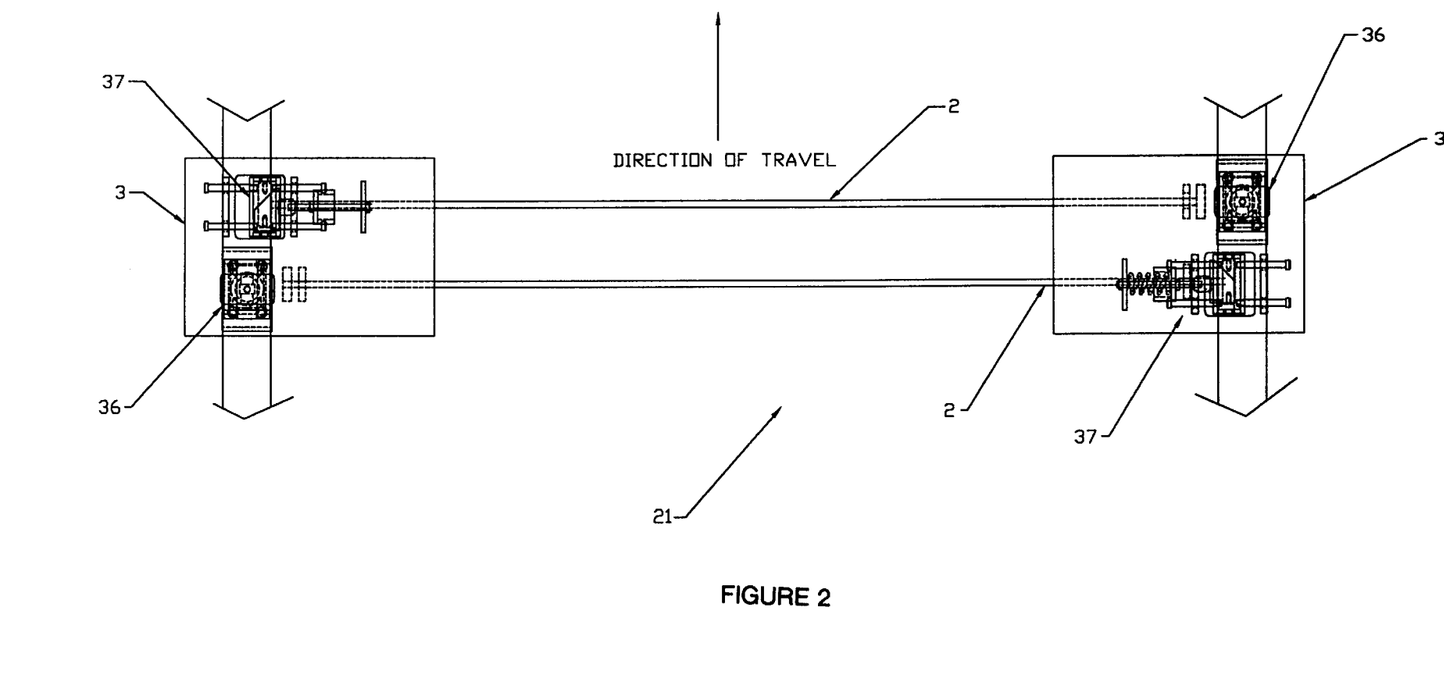
FIG. 2 is a plan view of an embodiment of the present invention shown without a main housing.

In another embodiment, shown in FIG. 2, the device 21 comprises four sensor assemblies: two vertical sensor assemblies 36 and two lateral sensor assemblies 37. Preferably, there is one vertical sensor assembly 36 and one lateral sensor assembly 37 on each side of the device 21. The assemblies are all disposed in a main housing (not shown in FIG. 2). A first lateral sensor assembly 37 and a first vertical sensor assembly 36 are defined as the sensor assemblies measuring friction on a first rail 40. Similarly, a second lateral assembly 37 and a second vertical assembly 36 are defined as the sensor assemblies measuring friction on a second rail 40. Using this embodiment, both top surface and gage face lubrication measurements can be made on each of the first and the second rails 40 simultaneously.

As seen in FIG. 2, the first lateral sensor assembly 37 and first vertical sensor assembly 36 are connected by the base plate 3 and the second lateral sensor assembly 37 and second vertical sensor assembly 36 are connected by means of another base plate 3 or other suitable structure. A frame (not shown) connects the base plates 3 of the first lateral and vertical sensor assemblies 37, 36 to the base plates 3 of the second lateral and vertical sensor assemblies 37, 36. This orientation of the four sensor assemblies permits the lateral sensor assemblies 37 to pass over track features such as gaps, frogs and switches. In particular, the lateral guard vertical plate 38 (FIG. 5), which is connected to the lateral sensor housing 11 by the lateral guard rod 2, engages the rail guards at switches or frogs and prevents extreme lateral movement.

The first lateral sensor assembly 37 may be directly across from and connected to the second lateral sensor assembly 37. Such an arrangement would require modifications to the lateral guard rod 2 to protect the assemblies 37 from gaps. For stretches of track lacking gaps and other discontinuities, the first and second lateral sensor assemblies 37 may be placed directly across from each other without a modified lateral guard rod 2 and be connected to one another by a frame, because when measuring such track, the lateral sensor assemblies 37 do not need to be protected from irregularities.

We claim:

1. A friction measuring device for use with a rail member, the rail member being of indefinite length and having a top surface and a gage surface, the top surface and the gage surface being generally perpendicular to each other, the device comprising:

a base frame adapted for movement along the rail member;

a vertical sensor assembly carried by the base frame, the vertical sensor assembly including a top shoe adapted for sliding contact with the rail member top face, an adjustable spring for biasing the top shoe against the rail member top face, a normal load sensor, and a tangential load sensor, the normal load sensor being adapted to measure the normal force of the top shoe against the rail member top face, the tangential load sensor being adapted to measure the tangential force exerted on the top shoe by the rail member top face as the top shoe slides along the rail member top face; and a lateral sensor assembly carried by the base frame, the lateral sensor assembly including a gage shoe adapted for sliding contact with the rail member gage face, an adjustable spring for biasing the gage shoe against the rail member gage face, a normal load sensor, and a tangential load sensor, the normal load sensor being adapted to measure the normal force of the gage shoe against the rail member gage face, the tangential load sensor being adapted to measure the tangential force exerted on the gage shoe by the rail member gage face as the gage shoe slides along the rail member gage face;

whereby in response to movement of the device along the rail member the coefficient of friction along the rail member top face and the rail member gage face is measured simultaneously.

2. The device of claim 1, including a top shoe housing sized to receive the top shoe, the top shoe housing being vertically moveable relative to the base frame.

3. The device of claim 1, including a top shoe housing sized to receive the top shoe, the top shoe housing being adapted to permit longitudinal movement of the top shoe relative to the top shoe housing as the device is moved along the rail member.

4. The device of claim 3, wherein the vertical sensor assembly tangential load sensor is disposed in the top shoe housing.

5. The device of claim 2, wherein the top shoe housing includes a vertical guide, and wherein the base plate includes a bushing sized to receive the vertical guide.

6. The device of claim 1, including a top shoe housing sized to receive the top shoe, and wherein the vertical sensor assembly spring operatively engages a top shaft, the top shaft being operatively coupled to the top shoe housing by the vertical sensor assembly normal load sensor.

7. The device of claim 6, wherein the first shaft is threaded and includes an adjustment nut, thereby permitting the biasing force of the first shoe against the rail member top face to be adjusted.

8. The device of claim 1, including a gage shoe housing, and wherein the gage shoe is mounted to a connector plate, a portion of the connector plate being disposed in the gage shoe housing, the gage shoe housing being horizontally moveable relative to the base frame.

9. The device of claim 8, wherein the gage shoe housing includes a horizontal guide, and wherein the base frame includes a bushing sized to receive the horizontal guide.

10. The device of claim 1, the rail member including an interruption and a track guard disposed generally adjacent the interruption, and wherein the gage shoe is operatively connected to a lateral guard rod, the lateral guard rod terminating in a guard plate, the guard rod and guard plate thereby preventing the gage shoe from engaging the rail member interruption.

11. The device of claim 8, wherein the gage shoe housing is sized to permit longitudinal movement of the connector plate and the gage shoe relative to the gage shoe housing as the device is moved along the rail member.

12. The device of claim 11, wherein the lateral sensor assembly tangential load sensor is disposed in the gage shoe housing.

13. The device of claim 1, wherein the gage shoe is mounted to a connector, and including a gage shoe housing sized to receive a portion of the connector, and wherein the lateral sensor assembly spring operatively engages a lateral shaft, the lateral shaft being operatively coupled to the gage shoe housing by the lateral sensor assembly normal load sensor.

14. The device of claim 13, wherein the lateral shaft is threaded and includes an adjustment nut, thereby permitting the biasing force of the gage shoe against the rail member gage face to be adjusted.

15. For use with a pair of spaced apart rail members, each of the rail members being of indefinite length and having a top surface and a gage surface, a device for simultaneously measuring the coefficient of friction on the top surface and the gage surface of each rail member as the device is moved along the rail members, the device comprising:

a base frame adapted for movement along the rail members;

first and second vertical sensor assemblies mounted to the base frame, each of the vertical sensor assemblies being generally aligned with and overlying the top surface of an adjacent one of the rail members, each vertical sensor assembly including a top shoe adapted for sliding contact with its adjacent rail member top face, an adjustable spring for biasing the top shoe against its adjacent rail member top face, a normal load sensor, and a tangential load sensor, the normal load sensor being adapted to measure the normal force of the top shoe against its adjacent rail member top face, the tangential load sensor being adapted to measure the tangential force exerted on the top shoe by its adjacent rail member top face as the top shoes slide along their adjacent rail member top face; and first and second lateral sensor assemblies mounted to the base frame, each of the lateral sensor assemblies including a gage shoe adapted for sliding contact with its adjacent rail member gage face, an adjustable spring for biasing the gage shoe against its rail member gage face, a normal load sensor, and a tangential load sensor, the normal load sensor being adapted to measure the normal force of the gage shoe against its rail member gage face, the tangential load sensor being adapted to measure the tangential force exerted on the gage shoe by its rail member gage face as the gage shoes slide along their adjacent rail member gage face;

thereby permitting simultaneous measurement of the coefficient of friction along the top face and the gage face of both rail members.

16. The device of claim 15, wherein each of the vertical sensor assemblies includes a top shoe housing sized to receive one of the top shoes, each top shoe housing being vertically moveable relative to the base frame.

17. The device of claim 16, wherein each top shoe housing is adapted to permit longitudinal movement of its top shoe relative to its corresponding housing as the device is moved along the rail members.

18. The device of claim 17, wherein each vertical sensor assembly tangential load sensor is disposed in a corresponding one of the top shoe housings.

19. The device of claim 16, wherein each the top shoe housing includes a vertical guide, and wherein the base plate includes a bushing sized to receive each of the vertical guides.

20. The device of claim 16, wherein each vertical sensor assembly spring operatively engages a top shaft, each top shaft being operatively coupled to its corresponding top shoe housing by a corresponding one of the vertical sensor assembly normal load sensors.

21. The device of claim 15, wherein each of the gage shoes is mounted to a connector member, a portion of each connector member being disposed in a gage shoe housing, each gage shoe housing being horizontally moveable relative to the base frame.

22. The device of claim 19, wherein each gage shoe housing includes a horizontal guide, and wherein the base frame includes bushings sized to receive the horizontal guides.

23. The device of claim 15, the rail member including intermittently spaced interruptions, and track guards disposed generally adjacent the interruptions, and wherein each of the gage shoes is operatively connected to a lateral guard rod, each lateral guard rod terminating in a guard plate, the guard rods and the guard plates thereby preventing their corresponding gage shoe from engaging the rail member interruptions.

24. The device of claim 21, wherein each gage shoe housing is adapted to permit longitudinal movement of its corresponding connector plate and gage shoe relative to the gage shoe housing as the device is moved along the rail member, and further wherein each lateral sensor assembly tangential load sensor is disposed in a corresponding one of the gage shoe housings.

25. A friction measuring device for use with a rail member, the rail member being of indefinite length and having a generally continuous surface, the device comprising:

a base frame adapted for movement along the rail member; and a sensor assembly carried by the base frame, the sensor assembly including:

a shoe adapted for direct sliding contact with the rail member surface at an interface;

means for biasing the shoe against the rail member surface;

a normal load sensor, the normal load sensor being adapted to measure the normal force of the shoe against the rail member surface; and a tangential load sensor, the tangential load sensor being adapted to measure the tangential force exerted on the shoe by the rail member surface as the shoe slides along the rail member surface;

thereby permitting direct measurement of the coefficient of friction at the interface between the shoe and the rail member surface in response to movement of the device along the rail member.

* * * * *